(12) United States Patent
Martin et al.

(10) Patent No.: US 7,410,648 B2
(45) Date of Patent: Aug. 12, 2008

(54) **POLYPEPTIDES OF *MORAXELLA (BRANHAMELLA) CATARRHALIS***

(75) Inventors: Denis Martin, St. Augustin-de-Desmaures (CA); Josée Hamel, Sillery (CA); Bernard R. Brodeur, Sillery (CA); Stéphane Rioux, Beauport (CA); Julie Couture, St-Augustin-de-Desmaures (CA)

(73) Assignee: ID Biomedical Corporation, Laval (CA)

( * ) Notice: Subject to any disclaimer, the term of this patent is extended or adjusted under 35 U.S.C. 154(b) by 396 days.

(21) Appl. No.: 10/495,643

(22) PCT Filed: Nov. 15, 2002

(86) PCT No.: PCT/CA02/01760

§ 371 (c)(1),
(2), (4) Date: Oct. 25, 2004

(87) PCT Pub. No.: WO03/043986

PCT Pub. Date: May 30, 2003

(65) Prior Publication Data

US 2005/0070691 A1 Mar. 31, 2005

Related U.S. Application Data

(60) Provisional application No. 60/331,441, filed on Nov. 16, 2001.

(51) Int. Cl.
*A61K 39/02* (2006.01)
*A61K 39/00* (2006.01)
*C07H 21/04* (2006.01)
*C07K 14/00* (2006.01)
*C12P 21/04* (2006.01)

(52) U.S. Cl. ............... 424/251.1; 424/234.1; 424/190.1; 424/184.1; 530/350; 530/300; 536/23.7; 536/23.4; 435/340; 435/331; 435/252.3; 435/69.7

(58) Field of Classification Search .............. 536/23.7, 536/23.4; 435/69.7, 252.3, 331, 340; 530/300, 530/350; 424/251.1, 234.1, 190.1, 184.1
See application file for complete search history.

(56) References Cited

U.S. PATENT DOCUMENTS 6,673,910 B1  1/2004  Breton

FOREIGN PATENT DOCUMENTS

| WO | 99/58563 A2 | 11/1999 |
|----|----|----|
| WO | 00/09694 A1 | 2/2000 |
| WO | 00/71724 A2 | 11/2000 |
| WO | WO 0078968 | 12/2000 |
| WO | 02/18595 A2 | 3/2002 |
| WO | 02/062378 A2 | 8/2002 |

OTHER PUBLICATIONS

Rudinger et al, Peptide Hormones, edited by Parsons, J.A., University Park Press, Jun. 1976.*
Roitt et al, 1998, Immunology, 4th ed, Mosby, London ,(p. 7.7-7.8).*
Bowie et al (Science, 1990, 247:1306-1310).*
Holmes (Exp. Opin.Invest. Drugs, 2001, 10(3):511-519).*
Herbert et al. (The Dictionary of Immunology, Academic Press, 4th edition, 1995, p. 58.*
Greenspan et al (Nature Biotechnology 7:936-937 (1999).*
McMichael J.C., "Vaccines for *Moraxella catarrhalis*," Vaccine, 2001, pp. S101-S107, vol. 19, XP004227957, ISSN: 0264-410X, the whole document.
McMichael J.C., "Progress toward the development of a vaccine to prevent *Moraxella (Branhamella) catarrhalis* infections," Microbes and Infection, Apr. 2000, pp. 561-568, vol. 2, No. 5, XP001118937, ISSN: 1286-4579, the whole document.
Jameson and Wolf, "The antigenic index: a novel algorithm for predicting antigenic determinants," Computer Application Bioscience, 4(1):181-186, 1988.
Wan et al., "Epitope Map for a Growth Hormone Receptor Agonist Monoclonal Antibody, MAb 263," Molecular Endocrinology, 17(11):2240-2250, 2003.

* cited by examiner

*Primary Examiner*—Shanon A. Foley
*Assistant Examiner*—Padma V Baskar
(74) *Attorney, Agent, or Firm*—Seed IP Law Group PLLC

(57) ABSTRACT

The present invention relates to polypeptides, more particularly polypeptides of *Moraxella (Branhamella) catarrhalis* which may be used to prevent, diagnose and/or treat *Moraxella (Branhamella) catarrhalis* infection.

11 Claims, 1 Drawing Sheet

Figure 1

```
  1 GTGGTGCTGG GCTTGGCATT GCTGCTTGTT CACCCCAATC TCCAACAGTC GCAGAACATC
 61 AGCCGCAACA ACAAGAACCT CTACAATACA CCAACGCTGA AGCACAAGCA CTTCAAGAGC
121 AAGCCGCCGC CTTACAAGCC CAAGCTGCCG AGCTTGAAAT GCAAGCTCAA GAAGCACAAG
181 CAGATGCCAG CCATGAAACC AAGGCAACTT CTGCCGATGG TAGCGGTGTC GGTAGCCTAC
241 TGGCAGGTGC TGCGGCAGGT GCTGCGGCAG GTTATGTTGC AAGCAAAGTT GCTGGTAATC
301 GTGCTGCTAC CGCTCAAGCT TCACAAACCC CCCAAACACC AACAACCACA CAACAACCAG
361 CACAAAATAA CCAACAAGCC ACCAACAGCA ATCGCCAAAG CCTCGCTCAA GCCACCCAAG
421 ACAACCGAGC TGGCACCACT CGCCAAGGTT TTGGTGCGAC AGGCGGTGCG ACAGGTTCGG
481 CCTCATGAAG CGTATCACTG TTGCACCACG ACCAGATTGG CAAAGCGAAA TGGCACGCAT
541 TGGCTTTAA (SEQ ID NO:1)
```

Figure 2

```
  1 VVLGLALLLV HPNLQQSQNI SRNNKNLYNT PTLKHKHFKS KPPPYKPKLP SLKCKLKKHK
 61 QMPAMKPRQL LPMVAVSVAY WQVLRQVLRQ VMLQAKLLVI VLLPLKLHKP PKHQQPHNNQ
121 HKITNKPPTA IAKASLKPPK TTELAPLAKV LVRQAVRQVR PHEAYHCCTT TRLAKRNGTH
181 WL* (SEQ ID NO:2)
```

Figure 3

```
  1 GTGAAATTTA AAACATTTGG ACTTATGGCA GCCATTGTTG GTACATTTAG TATCTCAGCT
 61 TGTAGCGGTC AAAACGAACA AAGCACAAAA GCCAGTGGTG ACACCTTGCG TATTGCGACC
121 GAAGGCACTT ATGCACCATT TAACTACACC AATCCAGATG GCAGTTTGGG CGGCTTTGAT
181 GTGGATATCG CCAATGCGTT ATGCAACAAA ATGCAAACCG AATGCCAAAT CATTGCCCAA
241 GATTGGGACG GTATTATACC AGCATTAAAA ACAGGTAAGT TTGATGCCAT TGTTGCAGCA
301 ATGTCAGTCA CCCCTGAGCG TAGTGAGCAG GTGGATTTTA GCGAGCCTTA TTTTGTCAAC
361 TCTTTGGTAT TTTTGGCAAA AAAGGTTCA AATTTTGATC CGAGCAGCAC CGATGCCATC
421 AATAATGCCA AAATTGTTGC TCAGCGTTCA ACCATCTCAA GTCAATGGTT AACCCAAACT
481 TATCCAAACA GCAAGCCACA GCTGTACGAT ACGCTGGACA ATGCTTTTAT TGATTTAGGT
541 AATGAGCGTG CTGACGCTAT GATTTCTGAC AAACTGCCAG CATTAACTTG GCTTAGCTCG
601 GACTTGGGTC AAAATTTTGA GATCAAAGGT GGGGACATTA ATATCAATGA TAAAGTCTCC
661 ATTGCTGTCG ATAAAGGCAA TACCGCACTA TTACAAAAAT TCAATGAGGC TTTGGCTGCA
721 ATCAAGGCTG ATGGCACCTA TAAACAAATT GTCATTAAGC ACTTTGGTGA AGCAGGTATG
781 CCAACTAATA TTGAATAA (SEQ ID NO:3)
```

Figure 4

```
  1 VKFKTFGLMA AIVGTFSISA CSGQNEQSTK ASGDTLRIAT EGTYAPFNYT NPDGSLGGFD
 61 VDIANALCNK MQTECQIIAQ DWDGIIPALK TGKFDAIVAA MSVTPERSEQ VDFSEPYFVN
121 SLVFLAKKGS NFDPSSTDAI NNAKIVAQRS TISSQWLTQT YPNSKPQLYD TLDNAFIDLG
181 NERADAMISD KLPALTWLSS DLGQNFEIKG GDININDKVS IAVDKGNTAL LQKFNEALAA
241 IKADGTYKQI VIKHFGEAGM PTNIE* (SEQ ID NO:4)
```

POLYPEPTIDES OF *MORAXELLA* (*BRANHAMELLA*) *CATARRHALIS*

CROSS REFERENCE TO RELATED APPLICATIONS

This application claims the benefit of U.S. Provisional application No. 60/331,441 filed Nov. 16, 2001.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 484112_430USPC_SEQUENCE_LISTING.txt. The text file is 8 KB, was created on Nov. 15, 2007, and is being submitted electronically via EFS-Web.

FIELD OF THE INVENTION

The present invention is related to polypeptides, more particularly SHB-MC100 and SHB-MC101 polypeptides of *Moraxella* (*Branhamella*) *catarrhalis* which may be used to prevent, diagnose and/or treat *Moraxella* (*Branhamella*) *catarrhalis* infection.

BACKGROUND OF THE INVENTION

*Moraxella* (*Branhamella*) *catarrhalis* is a Gram-negative *diplococcus* that causes respiratory tract infections in humans. *M. catarrhalis* is now accepted as the third most common cause of otitis media in infants and children, after *Streptococcus pneumoniae* and *Haemophilus influenzae*. *M. catarrhalis* has also been associated with several other types of infection, including sinusitis, persistent cough, and acute laryngitis.

Since approximately 90% of *M. catarrhalis* strains are resistant to antibiotics (β-lactamase positive) and that recurrent otitis media is associated with high morbidity, there is a need for the development of a vaccine that will protect individuals from *M. catarrhalis* infection. An infection by *M. catarrhalis* induces an immune response against antigens found at the surface of the bacterial cells. However, many of these surface proteins are still not characterized, nor has the immune response resulting in protection from infection by different strains been determined.

WO 00/78968 discloses nucleotide sequences from the genome of *Moraxella catarrhalis*.

To develop a vaccine that will protect individuals from *M. catarrhalis* infection, efforts have mainly been concentrated on outer membrane proteins such as the high-molecular-mass protein named ubiquitous surface protein A (UspA). This protein is considered a promising vaccine candidate because a monoclonal antibody and polyclonal antibodies were both shown to be bactericidal and protective in the murine pulmonary-clearance model. However, this protein was shown to be highly variable among the different strains of *M. catarrhalis*. In addition to this protein, other *M. catarrhalis* proteins have generated interest as potential vaccine candidates. The transferrin-binding protein, which possesses conserved epitopes, exposed on the bacterial surface. However, there was divergence in the degree of antibody cross-reactivity with the protein from one strain to another. Other investigators have also focused on the 45-kDa protein CD (OMP CD). This protein is highly conserved among strains of *M. catarrhalis*, however adults with chronic obstructive pulmonary disease show variability in the immune response against the OMP CD.

Therefore there remains an unmet need for *M. catarrhalis* polypeptides that may be used used to prevent, diagnose and/or treat *Moraxella* (*Branhamella*) *catarrhalis* infection.

SUMMARY OF THE INVENTION

According to one aspect, the present invention provides an isolated polynucleotide encoding a polypeptide having at least identity to a second polypeptide comprising a sequence chosen from SEQ ID Nos: 2, 4 or fragments or analogs thereof.

According to one aspect, the present invention relates to polypeptides comprising a sequence chosen from SEQ ID Nos: 2, 4 or fragments or analogs thereof.

In other aspects, there are provided polypeptides encoded by polynucleotides of the invention, pharmaceutical compositions, vectors comprising polynucleotides of the invention operably linked to an expression control region, as well as host cells transfected with said vectors and processes for producing polypeptides comprising culturing said host cells under conditions suitable for expression.

BRIEF DESCRIPTION OF THE DRAWINGS

FIG. 1 represents the DNA sequence of SHB-MC100 gene from *M. catarrhalis* strain ETSU C-2; SEQ ID NO: 1. The underlined portion of the sequence represents the region coding for the leader peptide.

FIG. 2 represents the amino acid sequence of SHB-MC100 polypeptide from *M. catarrhalis* strain ETSU C-2; SEQ ID NO: 2. The underlined sequence represents the 15 amino acid residues leader peptide.

FIG. 3 represents the DNA sequence of SHB-MC101 gene from *M. catarrhalis* strain ETSU C-2; SEQ ID NO: 3. The underlined portion of the sequence represents the region coding for the leader peptide.

FIG. 4 represents the amino acid sequence of SHB-MC101 polypeptide from *M. catarrhalis* strain ETSU C-2; SEQ ID NO: 4. The underlined sequence represents the 20 amino acid residues leader peptide.

DETAILED DESCRIPTION OF THE INVENTION

The present invention provides purified and isolated polynucleotides, which encode *Moraxella* polypeptides which may be used to prevent, diagnose and/or treat *Moraxella* infection.

According to one aspect, the present invention provides an isolated polynucleotide encoding a polypeptide having at least 70% identity to a second polypeptide comprising a sequence chosen from SEQ ID NOs: 2, 4 or fragments or analogs thereof.

According to one aspect, the present invention provides an isolated polynucleotide encoding a polypeptide having at least 80% identity to a second polypeptide comprising a sequence chosen from SEQ ID NOS: 2, 4 or fragments or analogs thereof.

According to one aspect, the present invention provides an isolated polynucleotide encoding a polypeptide having at least 90% identity to a second polypeptide comprising a sequence chosen from SEQ ID NOS: 2, 4 or fragments or analogs thereof.

According to one aspect, the present invention provides an isolated polynucleotide encoding a polypeptide having at least 95% identity to a second polypeptide comprising a sequence chosen from SEQ ID NOS: 2, 4 or fragments or analogs thereof.

According to one aspect, the present invention provides an isolated polynucleotide encoding a polypeptide having at least 98% identity to a second polypeptide comprising a sequence chosen from SEQ ID NOS: 2, 4 or fragments or analogs thereof.

According to one aspect, the present invention provides an isolated polynucleotide encoding a polypeptide having at least 70% identity to a second polypeptide comprising a sequence chosen from SEQ ID NOS: 2, 4.

According to one aspect, the present invention provides an isolated polynucleotide encoding a polypeptide having at least 80% identity to a second polypeptide comprising a sequence chosen from SEQ ID NOS: 2, 4.

According to one aspect, the present invention provides an isolated polynucleotide encoding a polypeptide having at least 90% identity to a second polypeptide comprising a sequence chosen from SEQ ID NOS: 2 or 4.

According to one aspect, the present invention provides an isolated polynucleotide encoding a polypeptide having at least 95% identity to a second polypeptide comprising a sequence chosen from SEQ ID NOS: 2 or 4.

According to one aspect, the present invention provides an isolated polynucleotide encoding a polypeptide having at least 98% identity to a second polypeptide comprising a sequence chosen from SEQ ID NOS: 2 or 4.

According to one aspect, the present invention relates to polypeptides which comprise an amino acid sequence selected from SEQ ID Nos: 2, 4 or fragments or analogs thereof.

According to one aspect, the present invention relates to polypeptides which comprise an amino acid sequence selected from SEQ ID Nos: 2 or 4.

According to one aspect, the present invention relates to polypeptides characterized by the amino acid sequence comprising an amino acid sequence selected from SEQ ID NOS: 2, 4 or fragments or analogs thereof.

According to one aspect, the present invention relates to polypeptides characterized by the amino acid sequence comprising an amino acid sequence selected from SEQ ID NOS: 2 or 4.

According to one aspect, the present invention provides a polynucleotide encoding an epitope bearing portion of a polypeptide comprising a sequence chosen from SEQ ID NOS: 2, 4 or fragments or analogs thereof.

According to one aspect, the present invention provides a polynucleotide encoding an epitope bearing portion of a polypeptide comprising a sequence chosen from SEQ ID NOS: 2 or 4.

According to one aspect, the present invention relates to epitope bearing portions of a polypeptide comprising a sequence chosen from SEQ ID NOS: 2, 4 or fragments or analogs thereof.

According to one aspect, the present invention relates to epitope bearing portions of a polypeptide comprising a sequence chosen from SEQ ID NOS: 2 or 4.

According to one aspect, the present invention provides an isolated polynucleotide comprising a polynucleotide chosen from:
(a) a polynucleotide encoding a polypeptide having at least 70% identity to a second polypeptide comprising a sequence chosen from: SEQ ID NOS: 2, 4 or fragments or analogs thereof;
(b) a polynucleotide encoding a polypeptide having at least 80% identity to a second polypeptide comprising a sequence chosen from: SEQ ID NOS: 2, 4 or fragments or analogs thereof;
(c) a polynucleotide encoding a polypeptide having at least 95% identity to a second polypeptide comprising a sequence chosen from: SEQ ID NOS: 2, 4 or fragments or analogs thereof;
(d) a polynucleotide encoding a polypeptide comprising a sequence chosen from: SEQ ID NOS: 2, 4 or fragments or analogs thereof;
(e) a polynucleotide encoding a polypeptide capable of raising antibodies having binding specificity for a polypeptide comprising a sequence chosen from: SEQ ID NOS: 2, 4 or fragments or analogs thereof;
(f) a polynucleotide encoding an epitope bearing portion of a polypeptide comprising a sequence chosen from SEQ ID NOS: 2, 4 or fragments or analogs thereof;
(g) a polynucleotide comprising a sequence chosen from SEQ ID NOS: 1, 3 or fragments or analogs thereof;
(h) a polynucleotide that is complementary to a polynucleotide in (a), (b), (c), (d), (e), (f) or (g).

According to one aspect, the present invention provides an isolated polynucleotide comprising a polynucleotide chosen from:
(a) a polynucleotide encoding a polypeptide having at least 70% identity to a second polypeptide comprising a sequence chosen from: SEQ ID NOS: 2 or 4;
(b) a polynucleotide encoding a polypeptide having at least 80% identity to a second polypeptide comprising a sequence chosen from: SEQ ID NOS: 2 or 4;
(c) a polynucleotide encoding a polypeptide having at least 95% identity to a second polypeptide comprising a sequence chosen from: SEQ ID NOS: 2 or 4;
(d) a polynucleotide encoding a polypeptide comprising a sequence chosen from: SEQ ID NOS: 2 or 4;
(e) a polynucleotide encoding a polypeptide capable of raising antibodies having binding specificity for a polypeptide comprising a sequence chosen from: SEQ ID NOS: 2 or 4;
(f) a polynucleotide encoding an epitope bearing portion of a polypeptide comprising a sequence chosen from SEQ ID NOS: 2 or 4;
(g) a polynucleotide comprising a sequence chosen from SEQ ID NOS: 1 or 3;
(h) a polynucleotide that is complementary to a polynucleotide in (a), (b), (c), (d), (e), (f) or (g).

According to one aspect, the present invention provides an isolated polypeptide comprising a polypeptide chosen from:
(a) a polypeptide having at least 70% identity to a second polypeptide comprising a sequence chosen from SEQ ID NOS: 2, 4 or fragments or analogs thereof;
(b) a polypeptide having at least 80% identity to a second polypeptide comprising a sequence chosen from SEQ ID NOS: 2, 4 or fragments or analogs thereof;
(c) a polypeptide having at least 95% identity to a second polypeptide comprising a sequence chosen from SEQ ID NOS: 2, 4 or fragments or analogs thereof;
(d) a polypeptide comprising a sequence chosen from SEQ ID NOS: 2, 4 or fragments or analogs thereof;
(e) a polypeptide capable of raising antibodies having binding specificity for a polypeptide comprising a sequence chosen from SEQ ID NOS: 2, 4 or fragments or analogs thereof;
(f) an epitope bearing portion of a polypeptide comprising a sequence chosen from SEQ ID NOS: 2, 4 or fragments or analogs thereof;
(g) the polypeptide of (a), (b), (c), (d), (e) or (f) wherein the N-terminal Met residue is deleted;

(h) the polypeptide of (a), (b), (c), (d), (e), (f) or (g) wherein the secretory amino acid sequence is deleted.

According to one aspect, the present invention provides an isolated polypeptide comprising a polypeptide chosen from:
(a) a polypeptide having at least 70% identity to a second polypeptide comprising a sequence chosen from SEQ ID NOS: 2 or 4;
(b) a polypeptide having at least 80% identity to a second polypeptide comprising a sequence chosen from SEQ ID NOS: 2 or 4;
(c) a polypeptide having at least 95% identity to a second polypeptide comprising a sequence chosen from SEQ ID NOS: 2 or 4;
(d) a polypeptide comprising a sequence chosen from SEQ ID NOS: 2 or 4;
(e) a polypeptide capable of raising antibodies having binding specificity for a polypeptide comprising a sequence chosen from SEQ ID NOS: 2 or 4;
(f) an epitope bearing portion of a polypeptide comprising a sequence chosen from SEQ ID NOS: 2 or 4;
(g) the polypeptide of (a), (b), (c), (d), (e) or (f) wherein the N-terminal Met residue is deleted;
(h) the polypeptide of (a), (b), (c), (d), (e), (f) or (g) wherein the secretory amino acid sequence is deleted.

Those skilled in the art will appreciate that the invention includes DNA molecules, i.e. polynucleotides, genes, their homologous genes and their complementary sequences that encode analogs such as mutants, variants, homologs and derivatives of such polypeptides, as described herein in the present patent application. The invention also includes RNA molecules corresponding to the DNA molecules of the invention. In addition to the DNA and RNA molecules, the invention includes the corresponding polypeptides and monospecific antibodies that specifically bind to such polypeptides.

In a further embodiment, the polypeptides in accordance with the present invention are antigenic.

In a further embodiment, the polypeptides in accordance with the present invention are immunogenic.

In a further embodiment, the polypeptides in accordance with the present invention can elicit an immune response in a host.

In a further embodiment, the present invention also relates to polypeptides which are able to raise antibodies having binding specificity to the polypeptides of the present invention as defined above.

An antibody that "has binding specificity" is an antibody that recognizes and binds the selected polypeptide but which does not substantially recognize and bind other molecules in a sample, e.g., a biological sample. Specific binding can be measured using an ELISA assay in which the selected polypeptide is used as an antigen.

In accordance with the present invention, "protection" in the biological studies is defined by a significant increase in the survival curve, rate or period. Statistical analysis using the Log rank test to compare survival curves, and Fisher exact test to compare survival rates and numbers of days to death, respectively, might be useful to calculate P values and determine whether the difference between the two groups is statistically significant. P values of 0.05 are regarded as not significant.

In an additional aspect of the invention there are provided antigenic/immunogenic fragments of the polypeptides of the invention, or of analogs thereof.

The fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a polypeptide or analog thereof as described herein. The present invention further provides fragments having at least 10 contiguous amino acid residues from the polypeptide sequences of the present invention. In one embodiment, at least 15 contiguous amino acid residues. In one embodiment, at least 20 contiguous amino acid residues.

The skilled person will appreciate that analogs of the polypeptides of the invention will also find use in the context of the present invention, i.e. as antigenic/immunogenic material. Thus, for instance proteins or polypeptides which include one or more additions, deletions, substitutions or the like are encompassed by the present invention.

As used herein, "fragments", "analogs" or "derivatives" of the polypeptides of the invention include those polypeptides in which one or more of the amino acid residues are substituted with a conserved or non-conserved amino acid residue (preferably conserved) and which may be natural or unnatural. In one embodiment, derivatives and analogs of polypeptides of the invention will have about 70% identity with those sequences illustrated in the figures or fragments thereof. That is, 70% of the residues are the same. In a further embodiment, polypeptides will have greater than 80% identity. In a further embodiment, polypeptides will have greater than 85% identity. In a further embodiment, polypeptides will have greater than 90% identity. In a further embodiment, polypeptides will have greater than 95% identity. In a further embodiment, polypeptides will have greater than 99% identity. In a further embodiment, analogs of polypeptides of the invention will have fewer than about 20 amino acid residue substitutions, modifications or deletions and more preferably less than 10.

In a further embodiment, polypeptides will have greater than 70% homology. In a further embodiment, polypeptides will have greater than 75% homology. In a further embodiment, polypeptides will have greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, derivatives and analogs of polypeptides of the invention will have less than about 20 amino acid residue substitutions, modifications or deletions and more preferably less than 10. Preferred substitutions are those known in the art as conserved i.e. the substituted residues share physical or chemical properties such as hydrophobicity, size, charge or functional groups.

These substitutions are those having a minimal influence on the secondary structure and hydropathic nature of the polypeptide.

Preferred substitutions are those known in the art as conserved, i.e. the substituted residues share physical or chemical properties such as hydrophobicity, size, charge or functional groups. These include substitutions such as those described by Dayhoff, M. in Atlas of Protein Sequence and Structure 5, 1978 and by Argos, P. in EMBO J. 8, 779-785, 1989. For example, amino acids, either natural or unnatural, belonging to one of the following groups represent conservative changes:
ala, pro, gly, gln, asn, ser, thr, val;
cys, ser, tyr, thr;
val, ile, leu, met, ala, phe;
lys, arg, orn, his;
and phe, tyr, trp, his.

The preferred substitutions also include substitutions of D-enantiomers for the corresponding L-amino acids.

In an alternative approach, the analogs could be fusion proteins, incorporating moieties which render purification easier, for example by effectively tagging the desired polypeptide. It may be necessary to remove the "tag" or it may e the case that the fusion polypeptide itself retains sufficient antigenicity to be useful.

The percentage of homology is defined as the sum of the percentage of identity plus the percentage of similarity or conservation of amino acid type.

In one embodiment, analogs of polypeptides of the invention will have about 70% homology with those sequences illustrated in the figures or fragments thereof. In a further embodiment, polypeptides will have greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, analogs of polypeptides of the invention will have fewer than about 20 amino acid residue substitutions, modifications or deletions and more preferably less than 10.

One can use a program such as the CLUSTAL program to compare amino acid sequences. This program compares amino acid sequences and finds the optimal alignment by inserting spaces in either sequence as appropriate. It is possible to calculate amino acid identity or homology for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

It is well known that it is possible to screen an antigenic polypeptide to identify epitopic regions, i.e. those regions which are responsible for the polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties.

In an additional aspect of the invention there are provided antigenic/immunogenic fragments of the proteins or polypeptides of the invention, or of analogs or derivatives thereof.

Thus, what is for analogs, derivatives and fragments is that they possess at least a degree of the antigenicity/immunogenicity of the protein or polypeptide from which they are derived.

Also included are polypeptides which have fused thereto other compounds which alter the polypeptides biological or pharmacological properties i.e. polyethylene glycol (PEG) to increase half-life; leader or secretory amino acid sequences for ease of purification; prepro- and pro-sequences; and (poly)saccharides.

Furthermore, in those situations where amino acid regions are found to be polymorphic, it may be desirable to vary one or more particular amino acids to more effectively mimic the different epitopes of the different *Moraxella* strains.

Moreover, the polypeptides of the present invention can be modified by terminal –NH$_2$ acylation (eg. by acetylation, or thioglycolic acid amidation, terminal carboxy amidation, e.g. with ammonia or methylamine) to provide stability, increased hydrophobicity for linking or binding to a support or other molecule.

Also contemplated are hetero and homo polypeptide multimers of the polypeptide fragments and analogs. These polymeric forms include, for example, one or more polypeptides that have been cross-linked with cross-linkers such as avidin/biotin, gluteraldehyde or dimethylsuperimidate. Such polymeric forms also include polypeptides containing two or more tandem or inverted contiguous sequences, produced from multicistronic RNAs generated by recombinant DNA technology.

In a further embodiment, the present invention also relates to chimeric polypeptides which comprise one or more polypeptides or fragments or analogs thereof as defined in the figures of the resent application.

In a further embodiment, the present invention also relates to chimeric polypeptides comprising two or more polypeptides having a sequence chosen from SEQ ID NOS: 2, 4 or fragments or analogs thereof; provided that the polypeptides are linked as to form a chimeric polypeptide.

In a further embodiment, the present invention also relates to chimeric polypeptides comprising two or more polypeptides comprising a sequence chosen from SEQ ID NOS: 2 or 4 provided that the polypeptides are linked as to form a chimeric polypeptide.

Preferably, a fragment, analog or derivative of a polypeptide of the invention will comprise at least one antigenic region i.e. at least one epitope.

In order to achieve the formation of antigenic polymers (i.e. synthetic multimers), polypeptides may be utilized having bishaloacetyl groups, nitroarylhalides, or the like, where the reagents being specific for thio groups. Therefore, the link between two mercapto groups of the different polypeptides may be a single bond or may be composed of a linking group of at least two, typically at least four, and not more than 16, but usually not more than about 14 carbon atoms.

In a particular embodiment, polypeptide fragments and analogs of the invention do not contain a methionine (Met) starting residue. Preferably, polypeptides will not incorporate a leader or secretory sequence (signal sequence). The signal portion of a polypeptide of the invention may be determined according to established molecular biological techniques. In general, the polypeptide of interest may be isolated from a *Moraxella* culture and subsequently sequenced to determine the initial residue of the mature protein and therefore the sequence of the mature polypeptide.

In another embodiment, the polypeptides of the invention may be lacking an N-terminal leader peptide, and/or a transmembrane domain and/or external loops and/or turns.

The present invention further provides a fragment of the polypeptide comprising substantially all of the extra cellular domain of a polypeptide which has at least 70% identify, preferably 80% identity, more preferably 95% identity, to a second polypeptide comprising a sequence chosen from Seq. ID Nos. 2, 4 or fragments or analogs thereof, over the entire length of said sequence.

It is understood that polypeptides can be produced and/or used without their start codon (methionine or valine) and/or without their leader peptide to favor production and purification of recombinant polypeptides. It is known that cloning genes without sequences encoding leader peptides will restrict the polypeptides to the cytoplasm of *E. coli* and will facilitate their recovery (Glick, B. R. and Pasternak, J. J. (1998) Manipulation of gene expression in prokaryotes. In "Molecular biotechnology: Principles and applications of recombinant DNA", 2nd edition, ASM Press, Washington D.C., p. 109-143).

According to another aspect of the invention, there are also provided (i) a composition of matter containing a polypeptide of the invention, together with a carrier, diluent, adjuvant or liposome; (ii) a pharmaceutical composition comprising a polypeptide of the invention and a carrier, diluent, adjuvant or liposome; (iii) a vaccine comprising a polypeptide of the invention and a carrier, diluent, adjuvant or liposome; (iv) a method for inducing an immune response against *Moraxella*, in a host, by administering to the host, an immunogenically effective amount of a polypeptide of the invention to elicit an immune response, e.g., a protective immune response to *Moraxella*; (v) a method for preventing and/or treating a *Moraxella* infection, by administering a prophylactic or therapeutic amount of a polypeptide of the invention to a host in need; and (vi) a method for preventing and/or treating a *Moraxella* infection, by administering a prophylactic or therapeutic amount of an antibody directed to a polypeptide of the invention to a host in need According to another aspect of the invention, there are also provided (i) a composition of matter containing a polynucleotide of the invention, together with a carrier, diluent, adjuvant or liposome; (ii) a pharmaceutical composition comprising a polynucleotide of the invention and a pharmaceutically acceptable carrier, diluent, adjuvant or liposome; (iii) a method for inducing an immune response against *Moraxella*, in a host, by administering to the host, an immunogenically effective amount of a polynucleotide of the invention to elicit an immune response, e.g., a protective immune response to *Moraxella*; and particularly, (iv) a method for preventing and/or treating a *Moraxella* infection, by administering a prophylactic or therapeutic amount of a polynucleotide of the invention to a host in need.

According to another aspect of the invention, there are also provided (i) a composition of matter containing a polypeptide of the invention, together with a liposome, carrier, diluent or adjuvant; (ii) a pharmaceutical composition comprising a polypeptide of the invention and a liposome, carrier, diluent or adjuvant; (iii) a vaccine comprising a polypeptide of the invention and a liposome, carrier, diluent or adjuvant; (iv) a method for inducing an immune response against *Moraxella*, in a host, by administering to the host, an immunogenically effective amount of a pharmaceutical composition of the invention to elicit an immune response, e.g., a protective immune response to *Moraxella*; and particularly, (v) a method for preventing and/or treating a *Moraxella* infection, by administering a prophylactic or therapeutic amount of a pharmaceutical composition of the invention to a host in need.

Before immunization, the polypeptides of the invention can also be coupled or conjugated to carrier proteins such as tetanus toxin, diphtheria toxin, hepatitis B virus surface antigen, poliomyelitis virus VP1 antigen or any other viral or bacterial toxin or antigen or any suitable proteins to stimulate the development of a stronger immune response. This coupling or conjugation can be done chemically or genetically. A more detailed description of peptide-carrier conjugation is available in Van Regenmortel, M. H. V., Briand J. P., Muller S., Plaué S., <<Synthetic Polypeptides as antigens>> in Laboratory Techniques in Biochemistry and Molecular Biology, Vol. 19 (ed.) Burdou, R. H. & Van Knippenberg P. H. (1988), Elsevier N.Y.

According to another aspect, there are provided pharmaceutical compositions comprising one or more Streptococcal polypeptides of the invention in a mixture with a pharmaceutically acceptable adjuvant. Suitable adjuvants include (1) oil-in-water emulsion formulations such as MF59™, SAF™, RIBI™; (2) Freund's complete or incomplete adjuvant; (3) salts i.e. $AlK(SO_4)_2$, $AlNa(SO_4)_2$, $AlNH_4(SO_4)_2$, $Al(OH)_3$, $AlPO_4$, silica, kaolin; (4) saponin derivatives such as STIMULON™ or particles generated therefrom such as ISCOMs (immunostimulating complexes); (5) cytokines such as interleukins, interferons, macrophage colony stimulating factor (M-CSF), tumor necrosis factor (TNF); (6) other substances such as carbon polynucleotides (e.g., poly IC and poly AU), detoxified cholera toxin (CTB), and *E. coli* heat labile toxin for induction of mucosal immunity. A more detailed description of adjuvant is available in a review by M. Z. I Khan et al. in Pharmaceutical Research, vol. 11, No. 1 (1994) pp 2-11, and also in another review by Gupta et al., in Vaccine, Vol. 13, No. 14, pp 1263-1276 (1995) and in WO 99/24578. Preferred adjuvants include QUILA™ (plant-derived saponin), QS21™, ALHYDROGEL™ (aluminum hydroxide) and ADJUPHOS™ (aluminum phosphate).

Pharmaceutical compositions of the invention may be administered parenterally by injection, rapid infusion, nasopharyngeal absorption, dermoabsorption, or buccal or oral.

The term "pharmaceutical composition" is also meant to include antibodies. In accordance with the present invention, there is also provided the use of one or more antibodies having binding specificity for the polypeptides of the present invention for the treatment or prophylaxis of *Moraxella* infection and/or diseases and symptoms mediated by *Moraxella* infection.

Pharmaceutical compositions of the invention are used for the prophylaxis of *Moraxella* infection and/or diseases and symptoms mediated by *Moraxella* infection as described in Manual of Clinical Microbiology, P. R. Murray (Ed, in chief), E. J. Baron, M. A. Pfaller, F. C. Tenover and R. H. Yolken. ASM Press, Washington, D.C. seventh edition, 1999, 1773p.

In one embodiment, pharmaceutical compositions of the present invention are used for the treatment or prophylaxis of otitis media, sinusitis, persistent cough, acute laryngitis, suppurative keratitis, conjunctivitis neonatorum. In one embodiment, pharmaceutical compositions of the invention are used for the treatment or prophylaxis of infection and/or diseases and symptoms mediated by *Moraxella*. In a further embodiment, the infection is caused by *Moraxella Catarrhalis*.

In a particular embodiment, pharmaceutical compositions are administered to those hosts at risk of *moraxella* infection such as infants, elderly and immunocompromised hosts.

As used in the present application, the term "host" includes mammals. In a further embodiment, the mammal is human.

Pharmaceutical compositions are preferably in unit dosage form of about 0.001 to 100 µg/kg (antigen/body weight) and more preferably 0.01 to 10 µg/kg and most preferably 0.1 to 1 µg/kg 1 to 3 times with an interval of about 1 to 6 week intervals between immunizations.

Pharmaceutical compositions are preferably in unit dosage form of about 0.1 µg to 10 mg and more preferably 1 µg to 1 mg and most preferably 10 to 100 µg 1 to 3 times with an interval of about 1 to 6 week intervals between immunizations.

According to another aspect, there are provided polynucleotides encoding polypeptides characterized by the amino acid sequence comprising SEQ ID NOS: 2, 4 or fragments or analogs thereof.

In one embodiment, polynucleotides are those illustrated in SEQ ID Nos: 1, 3 which may include the open reading frames (ORF), encoding the polypeptides of the invention.

It will be appreciated that the polynucleotide sequences illustrated in the figures may be altered with degenerate codons yet still encode the polypeptides of the invention. Accordingly the present invention further provides polynucleotides which hybridize to the polynucleotide sequences herein above described (or the complement sequences thereof) having 70% identity between sequences. In one embodiment, at least 80% identity between sequences. In one embodiment, at least 85% identity between sequences. In one embodiment, at least 90% identity between sequences. In a further embodiment, polynucleotides are hybridizable under stringent conditions i.e. having at least 95% identity. In a further embodiment, more than 97% identity.

Suitable stringent conditions for hybridization can be readily determined by one of skilled in the art (see for example Sambrook et al., (1989) Molecular cloning: A Laboratory Manual, 2$^{nd}$ ed, Cold Spring Harbor, N.Y.; Current Protocols in Molecular Biology, (1999) Edited by Ausubel F. M. et al., John Wiley & Sons, Inc., N.Y.).

In a further embodiment, the present invention provides isolated polynucleotides that hybridize under stringent conditions to either
(a) a DNA sequence encoding a polypeptide or
(b) the complement of a DNA sequence encoding a polypeptide;
wherein said polypeptide comprises a sequence chosen from SEQ ID NOS: 2, 4 or fragments or analogs thereof.

In a further embodiment, the present invention provides isolated polynucleotides that hybridize under stringent conditions to either
(a) a DNA sequence encoding a polypeptide or
(b) the complement of a DNA sequence encoding a polypeptide;
wherein said polypeptide comprises a sequence chosen from SEQ ID NOS: 2 or 4.

In a further embodiment, the present invention provides isolated polynucleotides that hybridize under stringent conditions to either
(a) a DNA sequence encoding a polypeptide or
(b) the complement of a DNA sequence encoding a polypeptide;
wherein said polypeptide comprises at least 10 contiguous amino acid residues from a polypeptide comprising a sequence chosen from SEQ ID NOS: 2, 4 or fragments or analogs thereof.

In a further embodiment, the present invention provides isolated polynucleotides that hybridize under stringent conditions to either
(a) a DNA sequence encoding a polypeptide or
(b) the complement of a DNA sequence encoding a polypeptide;
wherein said polypeptide comprises at least 10 contiguous amino acid residues from a polypeptide comprising a sequence chosen from SEQ ID NOS: 2 or 4.

In a further embodiment, polynucleotides are those encoding polypeptides of the invention illustrated in SEQ ID NOS: 2, 4.

In a further embodiment, polynucleotides are those illustrated in SEQ ID NOS: 1, 3 encoding polypeptides of the invention.

As will be readily appreciated by one skilled in the art, polynucleotides include both DNA and RNA.

The present invention also includes polynucleotides complementary to the polynucleotides described in the present application.

According to another aspect, there is provided a process for producing polypeptides of the invention by recombinant techniques by expressing a polynucleotide encoding said polypeptide in a host cell and recovering the expressed polypeptide product. Alternatively, the polypeptides can be produced according to established synthetic chemical techniques i.e. solution phase or solid phase synthesis of oligopeptides which are ligated to produce the full polypeptide (block ligation).

General methods for obtention and evaluation of polynucleotides and polypeptides are described in the following references: Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York; PCR Cloning Protocols, from Molecular Cloning to Genetic Engineering, Edited by White B. A., Humana Press, Totowa, N.J., 1997, 490 pages; Protein Purification, Principles and Practices, Scopes R. K., Springer-Verlag, New York, 3rd Edition, 1993, 380 pages; Current Protocols in Immunology, Edited by Coligan J. E. et al., John Wiley & Sons Inc., New York.

The present invention provides host cells transfected with vectors comprising the polynucleotides of the invention.

The present invention provides a process for producing a polypeptide comprising culturing a host cell of the invention under conditions suitable for expression of said polypeptide.

For recombinant production, host cells are transfected with vectors which encode the polypeptides of the invention, and then cultured in a nutrient media modified as appropriate for activating promoters, selecting transformants or amplifying the genes. Suitable vectors are those that are viable and replicable in the chosen host and include chromosomal, non-chromosomal and synthetic DNA sequences e.g. bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgarno sequence), and optionally an operator (control element). One can select individual components of the expression control region that are appropriate for a given host and vector according to established molecular biology principles (Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York). Suitable promoters include but are not limited to LTR or SV40 promoter, E. coli lac, tac or trp promoters and the phage lambda $P^L$ promoter. Vectors will preferably incorporate an origin of replication as well as selection markers, e.g., ampicillin resistance gene. Suitable bacterial vectors include pET, pQE70, pQE60, pQE-9, pD10 PHAGESCRIPT, psiX174, pBLUESCRIPT SK, pbsks, pNH8A, pNH16a, pNH18A, pNH46A, ptrc99a, pKK223-3, pKK233-3, pDR540, pRIT5 and eukaryotic vectors pBLUE-BACIII, pWLNEO, pSV2CAT, pOG44, pXT1, pSG, pSVK3, PBPV, pMSG and pSVL. Host cells may be bacterial (e.g., *E. coli, Bacillus subtilis, Streptomyces*); fungal (e.g., *Aspergillus niger, Aspergillus nidulins*); yeast (e.g., *Saccharomyces*) or eukaryotic (e.g., CHO, COS).

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide i.e. using ammonium sulfate or ethanol precipitation, acid extraction, anion or cation exchange chromatography, phosphocellulose chromatography, hydrophobic interaction chromatography, hydroxylapatite chromatography and lectin chromatography. Final purification may be achieved using HPLC.

The polypeptides may be expressed with or without a leader or secretion sequence. In the former case the leader may be removed using post-translational processing (see U.S.

Pat. Nos. 4,431,739; 4,425,437; and 4,338,397) or be chemically removed subsequent to purifying the expressed polypeptide.

According to a further aspect, the *Moraxella* polypeptides of the invention may be used in a diagnostic test for *Moraxella* infection, in particular *Moraxella* infection.

Several diagnostic methods for *Moraxella* infection in an host susceptible to *Moraxella* infection are possible, for example detecting *Moraxella* organism in a biological sample, the following procedure may be followed:
a) obtaining a biological sample from a host;
b) incubating an antibody or fragment thereof reactive with a *Moraxella* polypeptide of the invention with the biological sample to form a mixture; and
c) detecting specifically bound antibody or bound fragment in the mixture which indicates the presence of *Moraxella*.

Alternatively, a method for diagnostic for *Moraxella* infection in an host susceptible to *Moraxella* infection includes a method for the detection of antibody specific to a *Moraxella* antigen in a biological sample containing or suspected of containing said antibody may be performed as follows:
a) obtaining a biological sample from a host;
b) incubating one or more *Moraxella* polypeptides of the invention or fragments thereof with the biological sample to form a mixture; and
c) detecting specifically bound antigen or bound fragment in the mixture which indicates the presence of antibody specific to *Moraxella*.

One of skill in the art will recognize that this diagnostic test may take several forms, including an immunological test such as an enzyme-linked immunosorbent assay (ELISA), a radioimmunoassay or a latex agglutination assay, essentially to determine whether antibodies specific for the polypeptide are present in an organism.

The DNA sequences encoding polypeptides of the invention may also be used to design DNA probes for use in detecting the presence of *Moraxella* in a biological sample suspected of containing such bacteria. The detection method of this invention comprises:
a) obtaining the biological sample from a host;
b) incubating one or more DNA probes having a DNA sequence encoding a polypeptide of the invention or fragments thereof with the biological sample to form a mixture; and
c) detecting specifically bound DNA probe in the mixture which indicates the presence of *Moraxella* bacteria.

The DNA probes of this invention may also be used for detecting circulating *Moraxella* i.e. *Moraxella* nucleic acids in a sample, for example using a polymerase chain reaction, as a method of diagnosing *Moraxella* infections. The probe may be synthesized using conventional techniques and may be immobilized on a solid phase, or may be labelled with a detectable label. A preferred DNA probe for this application is an oligomer having a sequence complementary to at least about 6 contiguous nucleotides of the *Moraxella* polypeptides of the invention. In a further embodiment, the preferred DNA probe will be an oligomer having a sequence complementary to at least about 15 contiguous nucleotides of the *Moraxella* polypeptides of the invention. In a further embodiment, the preferred DNA probe will be an oligomer having a sequence complementary to at least about 30 contiguous nucleotides of the *Moraxella* polypeptides of the invention. In a further embodiment, the preferred DNA probe will be an oligomer having a sequence complementary to at least about 50 contiguous nucleotides of the *Moraxella* polypeptides of the invention.

Another diagnostic method for the detection of *Moraxella* in a host comprises:
a) labelling an antibody reactive with a polypeptide of the invention or fragment thereof with a detectable label;
b) administering the labelled antibody or labelled fragment to the host; and
c) detecting specifically bound labelled antibody or labelled fragment in the host which indicates the presence of *Moraxella*.

In a further aspect, polynucleotides encoding polypeptides of the invention, or fragments, analogs or derivatives thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

A further aspect of the invention is the use of the *Moraxella* polypeptides of the invention as immunogens for the production of specific antibodies for the diagnosis and in particular the treatment of *Moraxella* infection.

A further aspect of the invention is the use of the antibodies directed to the polypeptides of the invention for passive immunization. One could use the antibodies described in the present application. Suitable antibodies may be determined using appropriate screening methods, for example by measuring the ability of a particular antibody to passively protect against *moraxella* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *Moraxella* polypeptides but is preferably specific for one.

The use of a polynucleotide of the invention in genetic immunization will preferably employ a suitable delivery method or system such as direct injection of plasmid DNA into muscles [Wolf et al. H M G (1992) 1: 363; Turnes et al., Vaccine (1999), 17: 2089; Le et al., Vaccine (2000) 18: 1893; Alves et al., Vaccine (2001) 19: 788], injection of plasmid DNA with or without adjuvants [Ulmer et al., Vaccine (1999) 18: 18; MacLaughlin et al., J. Control Release (1998) 56: 259; Hartikka et al., Gene Ther. (2000) 7: 1171-82; Benvenisty and Reshef, PNAS USA (1986) 83:9551; Singh et al., PNAS USA (2000) 97: 811], targeting cells by delivery of DNA complexed with specific carriers [Wa et al., J Biol Chem (1989) 264: 16985; Chaplin et al., Infect. Immun. (1999) 67: 6434], injection of plasmid complexed or encapsulated in various forms of liposomes [Ishii et al., AIDS Research and Human Retroviruses (1997) 13: 142; Perrie et al., Vaccine (2001) 19: 3301], administration of DNA with different methods of bombardment [Tang et al., Nature (1992) 356: 152; Eisenbraun et al., DNA Cell Biol (1993) 12: 791; Chen et al., Vaccine (2001) 19: 2908], and administration of DNA with lived vectors [Tubulekas et al., Gene (1997) 190: 191; Pushko et al., Virology (1997) 239: 389; Spreng et al. FEMS (2000) 27: 299; Dietrich et al., Vaccine (2001) 19: 2506].

In a further aspect, the invention provides a method for prophylactic or therapeutic treatment of *Moraxella* infection in a host susceptible to *Moraxella* infection comprising administering to the host a prophylactic or therapeutic amount of a pharmaceutical composition of the invention.

In a further embodiment, the invention provides the use of a pharmaceutical composition of the invention in the manufacture of a medicament for the prophylactic or therapeutic treatment of *Moraxella* infection.

In a further embodiment, the invention provides a kit comprising a polypeptide of the invention for detection or diagnosis of *Moraxella* infection.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

digested with NdeI and NotI and purified from agarose gel using a QIAQUICK gel extraction kit (QIAGEN). The NdeI-NotI PCR products were ligated to the NdeI-NotI pET21b(+) expression vector. The ligated products were transformed into *E. coli* strain DH5α [Φ80dlacZΔM15Δ (lacZYA-argF) U169 endA1 recA1 hsdR17($r_K$-$m_K$+) deoR thi-1 supE44λ⁻ gyrA96 relA1] (GIBCO BRL, Gaithersburg, Md.) according to the method of Simanis (Hanahan, D. DNA Cloning, 1985, D. M. Glover (ed), pp. 109-135).

Recombinant pET21b(+) plasmid (rpET21b(+)) containing SHB-MC100 gene was purified using a Qiagen kit and DNA insert was sequenced (Taq Dye Deoxy Terminator Cycle Sequencing kit, ABI, Foster City, Calif.).

TABLE 1

Oligonucleotide primers used for PCR amplification of *M. catarrhalis* genes.

| Genes | Primers I.D. | Restriction site | Vector | Sequence | Sequence ID No |
|---|---|---|---|---|---|
| SHB-MC100 | DMAR529 | NdeI | pET21b (+) | 5'-GGGACTTCCATATGCAGTCGCAGAACATCAGCCG-3' | 5 |
| SHB-MC100 | DMAR530 | NotI | pET21b (+) | 5'-ATTATATAGCGGCCGCAAGCCAATGCGTGCCATTTC-3' | 6 |
| SHB-MC100 | RIOS199 | BglII | pCMV-GH | 5'-GGCAGATCTTGCAGTCGCAGAACATCAGCCG-3' | 7 |
| SHB-MC100 | RIOS200 | SalI | pCMV-GH | 5'-ACGCGTCGACTTAAAGCCAATGCGTGCCATTTC-3' | 8 |
| SHB-MC101 | DMAR614 | NdeI | pET21b (+) | 5'-CATTTAGTATCCATATGTGTAGCGGTCAAAACGAACAA-3' | 9 |
| SHB-MC101 | DMAR615 | XhoI | pET21b (+) | 5'-CAATCTTATCTCGAGTTCAATATTAGTTGGCATACCTGC-3' | 10 |
| SHB-MC101 | RIOS197 | BamHI | pCMV-GH | 5'-CTAGGATCCTTGTAGCGGTCAAAACGAACAA-3' | 11 |
| SHB-MC101 | RIOS198 | HindIII | pCMV-GH | 5'-CAGAAGCTTTTATTCAATATTAGTTGGCATACCTGC-3' | 12 |

EXAMPLE 1

This example illustrates the cloning and molecular characteristics of SHB-MC100 gene and corresponding polypeptide. The coding region of *M. catarrhalis* SHB-MC100 (SEQ ID NO: 1) gene was amplified by PCR (DNA Thermal Cycler GENEAMP PCR system 2400 Perkin Elmer, San Jose, Calif.) from genomic DNA of *M. catarrhalis* strain ETSU C-2 using the following oligos that contained base extensions for the addition of restriction sites NdeI (CATATG) and NotI (GCGGCCGC): DMAR529 (5'-GGGACTTCCATATG-CAGTCGCAGAACATCAGCCG-3') (SEQ ID NO:5) and DMAR503 (5'-ATTATATAGCGGCCGCAAGCCAAT-GCGTGCCATTTC-3'-) (SEQ ID NO:6). PCR products were purified from agarose gel using a QIAGEN, gel extraction kit following the manufacturer's instructions QIAGEN, Chatsworth, Calif.), and digested with NdeI and NotI (AMERSHAM PHARMACIA Biotech, Inc, baie d'Urf, Canada). The pET21b(+) vector (NOVAGEN, Madison, Wis.) was It was determined that the open reading frame (ORF) which codes for SHB-MC100 polypeptide contains 549-bp and encodes a 182 amino acid residues polypeptide with a predicted pI of 11.99 and a predicted molecular mass of 20828.17 Da. Analysis of the predicted amino acid residues sequence (SEQ ID NO:2) using the SPSCAN software (Wisconsin Sequence Analysis Package; Genetics Computer Group) suggested the existence of a 15 amino acid residues signal peptide (VVLGLALLLVHPNLQ) (SEQ ID NO:13), which ends with a cleavage site located between two glutamine residues.

To confirm the presence by PCR amplification of SHB-MC100 (SEQ ID NO:1) gene, the following 3 distinct *M. catarrhalis* strains were used: *M. catarrhalis* ETSU C-2, ETSU T-25, and ETSU 658 clinical isolates were provided by the East Tennessee State University. The *E. coli* XL1-Blue MRF' was used in these experiments as negative control. SHB-MC100 (SEQ ID NO:1) gene was amplified by PCR (DNA Thermal Cycler GENEAMP PCR system 2400 Perkin Elmer) from genomic DNA from the 3 *M. catarrhalis* strains, and the control *E. coli* strain using the oligonucleotides primers DMAR529 (SEQ ID NO:5) and DMAR530 (SEQ ID NO:6) (Table 1). PCR was performed with 5 cycles of 15 sec at 94° C., 30 sec at 47° C. and 90 sec at 72° C. followed by 30 cycles of 15 sec at 94° C., 30 sec at 60° C. and 90 sec at 72° C. and a final elongation period of 7 min at 72° C. The PCR products were size fractionated in 1% agarose gels and were visualized by ethidium bromide staining. The results of these PCR amplifications are presented in Table 2. The analysis of the amplification products revealed that SHB-MC100 (SEQ ID NO:1) gene was present in the genome of all of the 3 M. catarrhalis strains tested. No such product was detected when the control E. coli DNA was submitted to identical PCR amplifications with these oligonucleotide primers.

TABLE 2

Identification of M. catarrhalis genes by PCR amplification.

| Strain Identification | Identification by PCR amplification of | |
| --- | --- | --- |
| | SHB-MC100 | SHB-MC101 |
| ETSU C-2 | + | + |
| ETSU 658 | + | + |
| ETSU T-25 | + | + |
| E. coli | − | − |

EXAMPLE 2

This example illustrates the cloning and molecular characteristics of SHB-MC101 gene and corresponding polypeptide.

The coding region of M. catarrhalis SHB-MC101 (SEQ ID NO: 3) gene was amplified by PCR (DNA Thermal Cycler GENEAMP PCR system 2400 Perkin Elmer) from genomic DNA of M. catarrhalis strain ETSU C-2 using the following oligos that contained base extensions for the addition of restriction sites NdeI (CATATG) and XhoI (CTCGAG): DMAR614 (SEQ ID NO:9) and DMAR615 (SEQ ID NO:10), which are presented in Table 1. The methods used for cloning SHB-MC101 gene into an expression vector and sequencing are similar to the methods described in Example 1.

It was determined that the open reading frame (ORF) which codes for SHB-MC101 contains 798-bp and encodes a 265 amino acid residues polypeptide with a predicted pI of 4.48 and a predicted molecular mass of 28600.89 Da. Analysis of the predicted amino acid residues sequence (SEQ ID NO:4) using the Spscan software (Wisconsin Sequence Analysis Package; Genetics Computer Group) suggested the existence of a 20 amino acid residues signal peptide (VKFK-TFGLMAAIVGTFSISA) (SEQ ID NO:14), which ends with a cleavage site located between an alanine and a cysteine residues.

The SHB-MC101 gene was shown to be present after PCR amplification using the oligonucleotide primers DMAR614 and DMAR615 in the 3 M. catarrhalis strains tested (Table 2). The methods used for PCR amplification of the SHB-MC101 gene were similar to the methods presented in Example 1. No such product was detected when the control E. coli DNA was submitted to identical PCR amplification with these oligonucleotide primers.

EXAMPLE 3

This example illustrates the cloning of M. catarrhalis genes in CMV plasmid pCMV-GH.

The DNA coding regions of a M. catarrhalis polypeptides were inserted in phase downstream of a human growth hormone (hGH) gene which was under the transcriptional control of the cytomegalovirus (CMV) promoter in the plasmid vector pCMV-GH (Tang et al., Nature, 1992, 356: 152). The CMV promotor is non-functional plasmid in E. coli cells but active upon administration of the plasmid in eukaryotic cells. The vector also incorporated the ampicillin resistance gene.

The coding regions of SHB-MC100 (SEQ ID NO: 1) and SHB-MC101 (SEQ ID NO: 3) genes without their leader peptide regions were amplified by PCR (DNA Thermal Cycler GENEAMP PCR system 2400 Perkin Elmer) from genomic DNA of M. catarrhalis strain ETSU C-2 using oligonucleotide primers that contained base extensions for the addition of restriction sites BamHI (GGATCC), BglII (AGATCT), SalI (GTCGAC), or HindIII (AAGCTT) which are described in Table 1. The PCR products were purified from agarose gel using a QIAQUICK gel extraction kit (QIAGEN), and digested with restriction enzymes (AMERSHAM PHARMACIA Biotech, Inc). The pCMV-GH vector (Laboratory of Dr. Stephen A. Johnston, Department of Biochemistry, The University of Texas, Dallas, Tex.) was digested with BamHI, BglII, SalI, or HindIII and purified from agarose gel using the QIAQUICK gel extraction kit (QIAGEN). The digested DNA fragments were ligated to the digested PCMV-GH vector to create the hGH-SHB-MC100 and hGH-SHB-MC101 fusion polypeptides under the control of the CMV promoter. The ligated products were transformed into E. coli strain DH5Δ [Φ80dlacZΔM15 Δ (lacZYA-argF) U169 endA1 recA1 hsdR17 ($r_K^-m_K^+$) deoR thi-1 supE44 λ$^-$ gyrA96 relA1] (GIBCO BRL) according to the method of Simanis (Hanahan, D. DNA Cloning, 1985, D. M. Glover (ed), pp. 109-135). The recombinant pCMV plasmids were purified using a QIAGEN kit, and the nucleotide sequences of the DNA inserts were verified by DNA sequencing.

EXAMPLE 4

This example illustrates the use of DNA to elicit an immune response to M. catarrhalis polypeptide antigens.

A group of 8 female BALB/c mice (Charles River, St-Constant, Qubec, Canada) are immunized by intramuscular injection of 100 µl three times at two- or three-week intervals with 50 µg of recombinant PCMV-GH encoding SHB-MC100 (SEQ ID NO: 1) and SHB-MC101 (SEQ ID NO: 3) genes in presence of 50 µg of granulocyte-macrophage colony-stimulating factor (GM-CSF)-expressing plasmid pCMV-GH-GM-CSF (Laboratory of Dr. Stephen A. Johnston, Department of Biochemistry, The University of Texas, Dallas, Tex.). As control, a group of mice are injected with 50 µg of pCMV-GH in presence of 50 µg of pCMV-GH-GM-CSF. Blood samples are collected from the orbital sinus prior to each immunization and seven days following the third injection. Serum antibody responses are determined by ELISA using the corresponding His-Tag labeled M. catarrhalis recombinant polypeptides as coating antigen. The production and purification of these His-tag labeled M. catarrhalis recombinant polypeptides are presented in Example 5.

EXAMPLE 5

This example illustrates the production and purification of M. catarrhalis recombinant polypeptides.

The recombinant pET21 plasmid with SHB-MC100 (SEQ ID NO: 1) and SHB-MC101 (SEQ ID NO: 3) genes were used to transform by electroporation (GENE PULSER II apparatus, BIO-RAD Labs, Mississauga, Canada) E. coli strain BL21 (DE3) [F$^-$ ompT hsdS$_B$(r$^-_B$m$^-_B$) gal dcm (DE3)] (NOVAGEN). In this strain of E. coli, the T7 promoter controlling expression of the recombinant polypeptide is specifically recognized by the T7 RNA polymerase (present on the λDE3 prophage) whose gene is under the control of the lac promotor which is inducible by isopropyl-β-d-thio-galactopyranoside (IPTG). The transformant BL21(DE3)/rpET21 was grown at 37° C. with agitation at 250 rpm in LB broth (peptone 10 g/L, yeast extract 5 g/L, NaCl 10 g/L) containing 100 µg of carbenicillin (Sigma-Aldrich Canada Ltd., Oakville, Canada) per ml until the $A_{600}$ reached a value of 0.5. In order to induce the production of His-tagged *M. catarrhalis* recombinant polypeptides, the cells were incubated for 3 additional hours in the presence of IPTG at a final concentration of 1 mM. Induced cells from a 500 ml culture were pelleted by centrifugation and frozen at −70° C.

The purification of the SHB-MC100 His-tagged recombinant polypeptide from the non-soluble fraction of IPTG-induced BL21 (DE3)/rpET21b(+) was done by affinity chromatography based on the properties of the His.Tag sequence (6 consecutive histidine residues) to bind to divalent cations ($Ni^{2+}$) immobilized on the His.Bind metal chelation resin. Briefly, the pelleted cells obtained from a 500 mL culture induced with IPTG was resuspended in lysis buffer (20 mM Tris, 500 mM NaCl, 10 mM imidazole, pH 7.9) containing 6M Guanidine-HCl, sonicated and centrifuged at 12,000×g for 20 min to remove debris. The supernatant was incubated with Ni-NTA agarose resin (QIAGEN) for 45 min at 4° C. The SHB-MC100 His-tagged recombinant polypeptide was eluted from the resin with a solution containing 6M Guanidine-HCl and 250 mM imidazole-500 mM NaCl-20 mM Tris, pH 7.9. The removal of the salt and imidazole from the samples was done by dialysis against 10 mM Tris and 0.9% NaCl, pH 7.9 overnight at 4° C. The amount of recombinant polypeptide was estimated by MICROBCA (quantitative protein assay) (Pierce, Rockford, Ill.).

The purification of the recombinant polypeptide SHB-MC101 from the soluble cytoplasmic fraction of IPTG-induced BL21(DE3)/rpET21b (+) was done as described above using the buffers without Guanidine-HCl.

EXAMPLE 6

This example illustrates the reactivity of the His-tagged *M. catarrhalis* recombinant SHB-MC100 polypeptide with antibodies present in human palatine tonsils and sera collected from mice after immunization with *M. catarrhalis* antigenic preparations.

As shown in Table 3, SHB-MC100 His-tagged recombinant polypeptide was recognized in immunoblots by the antibodies present in the human palatine tonsils. It indicates that humans, who are normally in contact with *M. catarrhalis* do develop antibodies that are specific to this polypeptide. These particular human antibodies might be implicated in the protection against *M. catarrhalis* infection. In addition, immunoblots also revealed that sera collected from mice immunized with *M. catarrhalis* antigenic preparation enriched membrane polypeptides which induced significant lung clearance in a mouse model also developed antibodies that recognized this polypeptide. These results indicate that this polypeptide was present in *M. catarrhalis* antigenic preparation that protected mice against infection and that it induced antibodies that reacted with the corresponding SHB-MC100 His-tagged recombinant polypeptide.

TABLE 3

Reactivity in immunoblots of antibodies present in human palatine tonsils and sera collected from mice after immunization with *M. catarrhalis* antigenic preparations with *M. catarrhalis* His-tagged fusion recombinant SHB-MC100 polypeptide.

| Purified recombinant polypeptide I.D.[1] | Apparent molecular weight (kDa)[2] | Reactivity in immunoblots with Human palatine tonsils[3] | Mouse sera[4] |
|---|---|---|---|
| SHB-MC100 | 25 | + | + |

[1]His-tagged recombinant polypeptide produced and purified as described in Example 5 was used to perform the immunoblots.
[2]Molecular weight of the His-tagged recombinant polypeptide was estimated after SDS-PAGE.
[3]Extracts from human palatine tonsils were not diluted in order to perform the immunoblots.
[4]Mouse sera collected after immunization with *M. catarrhalis* antigenic preparations enriched membrane polypeptides were pooled and diluted 1/500 to perform the immunoblots. These mice were protected against *M. catarrhalis* challenge.

EXAMPLE 7

This example illustrates the accessibility to antibodies of the SHB-MC100 and SHB-MC101 polypeptides at the surface of *M. catarrhalis* strain.

Bacteria were grown in Brain Heart Infusion (BHI) broth containing 1% dextrose at 37° C. in a 8% $CO_2$ atmosphere to give an $OD_{490nm}$ of 0.650 (~$10^8$ CFU/ml). Dilutions of anti-SHB-MC100 or anti-SHB-MC101 or control sera were then added and allowed to bind to the cells, which were incubated for 2 h at 4° C. with rotation. Samples were washed 4 times in blocking buffer [phosphate-buffered saline (PBS) containing 2% bovine serum albumin (BSA)], and then 1 ml of goat fluorescein (FITC)-conjugated anti-mouse IgG Fc (gamma) fragment specific diluted in blocking buffer was added. After an additional incubation of 60 min at room temperature with rotation in the dark, samples were washed 4 times in blocking buffer and fixed with 0.25% formaldehyde in PBS buffer for 18 h at 4° C. Cells were kept in the dark at 4° C. until analyzed by flow cytometry (Epics® XL; BECKMAN COULTER, Inc.). Flow cytometric analysis revealed that SHB-MC100- and SHB-MC101-specific antibodies efficiently recognized their corresponding surface exposed epitopes on the *M. catarrhalis* heterologous strain ETSU 658 tested (Table 4). It was determined that more than 70% of the 10,000 *Moraxella* cells analyzed were labeled with the antibodies present in the SHB-MC100- and SHB-MC101-specific sera. These observations clearly demonstrate that the SHB-MC100 and SHB-MC101 polypeptides are accessible at the surface, where they can be easily recognized by antibodies. Anti-*M. catarrhalis* antibodies were shown to play an important role in the protection against *M. catarrhalis* infection.

TABLE 4

Evaluation of the attachment of SHB-MC100- and SHB-MC101-specific antibodies at the surface of intact cells of *M. catarrhalis* strain ETSU-658.

| Serum Identification | Fluorescence Index[2] | % of labeled cells[3] |
|---|---|---|
| Pool of SHB-MC100-specific sera[1] | 10.0 | 85.9 |
| Pool of SHB-MC101-specific sera | 6.1 | 70.7 |

TABLE 4-continued

Evaluation of the attachment of SHB-MC100- and SHB-MC101-specific antibodies at the surface of intact cells of *M. catarrhalis* strain ETSU-658.

| Serum Identification | Fluorescence Index[2] | % of labeled cells[3] |
|---|---|---|
| Pool of negative control sera[4] | 1.0 | 1.0 |
| Positive control serum[5] | 22.5 | 72.4 |

[1]The mice were injected subcutaneously five times at two-week intervals with 20 µg of purified recombinant polypeptides mixed with 10 µg of QUILA ™ (plant-derived saponin) adjuvant (Cedarlane Laboratories, Hornby, Canada). The sera were diluted 1/50.
[2]The fluorescence index was calculated as the median fluorescence value obtained after labeling the cells with an immune serum divided by the fluorescence value obtained for a control mouse serum. A fluorescence value of 1 indicated that there was no binding of antibodies at the surface of intact *Moraxella* cells.
[3]% of labeled cells out of the 10,000 cells analyzed.
[4]Sera collected from unimmunized or sham-immunized mice were pooled, diluted 1/50, and used as negative controls for this assay.
[5]Serum obtained from a mouse immunized with 20 µg of purified outer membrane polypeptides from *M. catarrhalis* strain ETSU-658 was diluted 1/1000 and was used as a positive control for the assay.

EXAMPLE 8

This example illustrates the bactericidal activities of anti-recombinant polypeptide mouse sera.

Bacteria are plated on chocolate agar plate and incubated at 37° C. in a 8% $CO_2$ atmosphere for 16 h. Bacterial cells are then resuspended in bacteriolysis buffer [10% Hanks' Balanced Salt Solution (HBSS) and 1% hydrolyzed casein, pH 7.3] to an $OD_{490nm}$ of 0.25 and diluted to $8 \times 10^4$ CFU/ml. The bactericidal assay is performed by mixing 25 µl of the bacterial suspension with 50 µl of diluted heat-inactivated test serum and 15 µl of HBSS and incubating for 15 min at 37° C., 8% $CO_2$ with agitation (200 rpm). The rabbit complement-containing serum is then added to a final concentration of 10%, and the mixture is incubated for an additional 60 min at 37° C., 8% $CO_2$ with agitation (200 rpm). At the end of the incubation period, the number of viable bacteria is determined by plating 10 µl of the assay mixture on chocolate agar plate. The plates are incubated at 37° C. in an 8% $CO_2$ atmosphere for 18-24 h. The control consists of bacteria incubated with heat-inactivated sera collected from mice before immunization and rabbit complement. The *M. catarrhalis* strain ETSU 658 is used to evaluate the bactericidal activity of the sera. The bactericidal titer is determined as the highest serum dilution resulting in killing of 50% or more of the bacteria compared to the control.

EXAMPLE 9

This example illustrates the protection of mice against *M. catarrhalis* infection induced by immunization with purified recombinant polypeptides.

Groups of 8 female BALB/c mice (Charles River) were immunized subcutaneously five times at two-week intervals with 20 µg of either recombinant SHB-MC100 or SHB-MC101 polypeptides in presence of 10% QUILA™ (plant-derived saponin) adjuvant (Cedarlane Laboratories Ltd, Hornby, Canada) or, as control, with QUILA™ adjuvant alone in PBS. Blood samples were collected from the orbital sinus on day 0, 14, 28, 42, and 56 prior to each immunization and 14 days (day 70) following the fifth injection. One week later the mice were challenged intrapulmonary with approximately $1 \times 10^6$ CFU of the *M. catarrhalis* heterologous strain ETSU 658. Samples of the *M. catarrhalis* challenge inoculum were plated on chocolate agar plates to determine the CFU and to verify the challenge dose. Mice were killed by an intraperitoneal injection of sodium pentobarbital (Luthanyl™) 5 h after infection. The intact lungs were excised and homogenised in a tissue homogeniser. The lung homogenate was assessed for bacterial clearance by plating of serial dilutions for CFU determination. As shown in Table 5, the number of bacteria recovered at 5 h postchallenge was significantly reduced for the groups immunized with either SHB-MC100 or SHB-MC101 polypeptides compared to the control group. Thus, immunization with recombinant SHB-MC100 and SHB-MC101 polypeptides promoted rapid clearance of a heterologous strain of *M. catarrhalis* from lungs of mice.

TABLE 5

Pulmonary clearance of *Moraxella catarrhalis* by mice immunized with either purified recombinant SHB-MC100 or SHB-MC101 polypeptides

| Antigen | Bacterial recovery from control group (CFU/ml of lung homogenate)[a] | Bacterial recovery from immunized group (CFU/ml of lung homogenate)[b] | Bacterial clearance (%)[c] |
|---|---|---|---|
| SHB-MC100 | $2.4 \times 10^5 \pm 1.5 \times 10^5$ | $4.7 \times 10^4 \pm 4.7 \times 10^4$ | 80.4[d] |
| SHB-MC101 | $2.4 \times 10^5 \pm 1.5 \times 10^5$ | $7.6 \times 10^4 \pm 8.9 \times 10^4$ | 68.3[e] |

[a]Means ± standard deviations for seven mice.
[b]Means ± standard deviations for eight mice.
[c]Mice were challenged intrapulmonary with $1 \times 10^6$ CFU of bacteria, and viable bacteria were recovered from lung 5 h after challenge. The number is the percentage of bacteria cleared from immunized mice compared with that of the control.
[d]$P = 0.0030$; significance was determined using Mann-Whitney nonparametric analysis.
[e]$P = 0.0379$; significance was determined using Mann-Whitney nonparametric analysis.

What is claimed is:

1. An isolated polypeptide consisting of an amino acid sequence at least 90% identical to the amino acid sequence set forth as SEQ ID NO:2, wherein the polypeptide is capable of eliciting an antibody that specifically bonds to a protein consisting of the amino acid sequence set forth as SEQ ID NO:2, and wherein the polypeptide is capable of eliciting an immune response against *Moraxella catarrhalis*.

2. The isolated polypeptide according to claim 1 consisting of an amino acid sequence at least 95% identical to the amino sequence set forth as SEQ ID NO:2.

3. The polypeptide according to claim 1 consisting of an amino acid sequence at least 99% identical to the amino acid sequence set forth as SEQ ID NO:2.

4. The polypeptide according to claim 1 wherein the polypeptide consists of an amino sequence identical to the sequence set forth as SEQ ID NO:2.

5. An isolated polypeptide consisting of an amino acid sequence at least 95% identical to the amino acid sequence set forth as SEQ ID NO:2 from which the signal peptide consisting of the amino acid sequence set forth as SEQ ID NO:13 id deleted, where the polypeptide is capable of eliciting an antibody that specifically binds to a protein consisting of the amino acid sequence set forth as SEQ ID NO:2, and wherein the polypeptide is capable of an immune response against *Moraxella catarrhalis*.

6. The polypeptide according to claim 5 consisting of an amino acid sequence at least 99% identical to the amino acid sequence set forth as SEQ ID NO:2 from which the signal peptide sequence is deleted.

7. The polypeptide according to claim 5 consisting of the amino acid sequence set forth as SEQ ID NO:2 from which the signal peptide sequence is deleted.

8. An isolated polypeptide consisting of the amino acid sequence set forth as SEQ ID NO:2 from which the N-terminal valine residue is deleted, wherein the polypeptide is capable of eliciting an antibody that specifically binds to a protein consisting of the amino acid sequence ser forth as SEQ ID NO:2, and wherein the polypeptide is capable of eliciting an immune response against *Moraxella catarrhalis*.

9. A pharmaceutical composition comprising a polypeptide according to any one of claims 1, 2, and 3-8 and a pharmaceutically acceptable carrier, diluent or adjuvant.

10. A pharmaceutical composition comprising a polypeptide according to any one of claims 1, 2, and 3-8 and a liposome.

11. A kit comprising a polypeptide according to either claim 4 or claim 7 for detection or diagnosis of *Moraxella catarrhalis* infection.

\* \* \* \* \*

SEQUENCE LISTING

<160> NUMBER OF SEQ ID NOS: 12

<210> SEQ ID NO 1
<211> LENGTH: 549
<212> TYPE: DNA
<213> ORGANISM: Moraxella catarrhalis

<400> SEQUENCE: 1
gtggtgctgg gcttggcatt gctgcttgtt caccccaatc tccaacagtc gcagaacatc        60

-continued

```
agccgcaaca acaagaacct ctacaataca ccaacgctga agcacaagca cttcaagagc    120
aagccgccgc cttacaagcc caagctgccg agcttgaaat gcaagctcaa gaagcacaag    180
cagatgccag ccatgaaacc aaggcaactt ctgccgatgg tagcggtgtc ggtagcctac    240
tggcaggtgc tgcggcaggt gctgcggcag gttatgttgc aagcaaagtt gctggtaatc    300
gtgctgctac cgctcaagct tcacaaaccg cccaaacacc aacaaccaca caacaaccag    360
cacaaaataa ccaacaagcc accaacagca atcgccaaag cctcgctcaa gccacccaag    420
acaaccgagc tggcaccact cgccaaggtt ttggtgcgac aggcggtgcg acaggttcgg    480
cctcatgaag cgtatcactg ttgcaccacg accagattgg caaagcgaaa tggcacgcat    540
tggctttaa                                                            549
```

<210> SEQ ID NO 2
<211> LENGTH: 182
<212> TYPE: PRT
<213> ORGANISM: Moraxella catarrhalis

<400> SEQUENCE: 2

```
Val Val Leu Gly Leu Ala Leu Leu Leu Val His Pro Asn Leu Gln Gln
1               5                   10                  15

Ser Gln Asn Ile Ser Arg Asn Asn Lys Asn Leu Tyr Asn Thr Pro Thr
            20                  25                  30

Leu Lys His Lys His Phe Lys Ser Lys Pro Pro Pro Tyr Lys Pro Lys
        35                  40                  45

Leu Pro Ser Leu Lys Cys Lys Leu Lys Lys His Lys Gln Met Pro Ala
    50                  55                  60

Met Lys Pro Arg Gln Leu Leu Pro Met Val Ala Val Ser Val Ala Tyr
65                  70                  75                  80

Trp Gln Val Leu Arg Gln Val Leu Arg Gln Val Met Leu Gln Ala Lys
                85                  90                  95

Leu Leu Val Ile Val Leu Leu Pro Leu Lys Leu His Lys Pro Pro Lys
            100                 105                 110

His Gln Gln Pro His Asn Asn Gln His Lys Ile Thr Asn Lys Pro Pro
        115                 120                 125

Thr Ala Ile Ala Lys Ala Ser Leu Lys Pro Pro Lys Thr Thr Glu Leu
    130                 135                 140

Ala Pro Leu Ala Lys Val Leu Val Arg Gln Ala Val Arg Gln Val Arg
145                 150                 155                 160

Pro His Glu Ala Tyr His Cys Cys Thr Thr Thr Arg Leu Ala Lys Arg
                165                 170                 175

Asn Gly Thr His Trp Leu
            180
```

<210> SEQ ID NO 3
<211> LENGTH: 798
<212> TYPE: DNA
<213> ORGANISM: Moraxella catarrhalis

<400> SEQUENCE: 3

```
gtgaaattta aaacatttgg acttatggca gccattgttg gtacatttag tatctcagct     60
tgtagcggtc aaaacgaaca aagcacaaaa gccagtggtg acaccttgcg tattgcgacc    120
gaaggcactt atgcaccatt taactacacc aatccagatg gcagtttggg cggctttgat    180
gtggatatcg ccaatgcgtt atgcaacaaa atgcaaaccg aatgccaaat cattgcccaa    240
gattgggacg gtattatacc agcattaaaa acaggtaagt ttgatgccat tgttgcagca    300
```

-continued

```
atgtcagtca cccctgagcg tagtgagcag gtggatttta gcgagcctta ttttgtcaac    360
tctttggtat ttttggcaaa aaaaggttca aattttgatc cgagcagcac cgatgccatc    420
aataatgcca aaattgttgc tcagcgttca accatctcaa gtcaatggtt aacccaaact    480
tatccaaaca gcaagccaca gctgtacgat acgctggaca atgcttttat tgatttaggt    540
aatgagcgtg ctgacgctat gatttctgac aaactgccag cattaacttg gcttagctcg    600
gacttgggtc aaaattttga gatcaaaggt ggggacatta atatcaatga taaagtctcc    660
attgctgtcg ataaaggcaa taccgcacta ttacaaaaat tcaatgaggc tttggctgca    720
atcaaggctg atggcaccta taacaaattg tcattaagc actttggtga agcaggtatg    780
ccaactaata ttgaataa                                                  798
```

<210> SEQ ID NO 4
<211> LENGTH: 265
<212> TYPE: PRT
<213> ORGANISM: Moraxella catarrhalis

<400> SEQUENCE: 4

```
Val Lys Phe Lys Thr Phe Gly Leu Met Ala Ala Ile Val Gly Thr Phe
1               5                   10                  15

Ser Ile Ser Ala Cys Ser Gly Gln Asn Glu Gln Ser Thr Lys Ala Ser
            20                  25                  30

Gly Asp Thr Leu Arg Ile Ala Thr Glu Gly Thr Tyr Ala Pro Phe Asn
        35                  40                  45

Tyr Thr Asn Pro Asp Gly Ser Leu Gly Gly Phe Asp Val Asp Ile Ala
    50                  55                  60

Asn Ala Leu Cys Asn Lys Met Gln Thr Glu Cys Gln Ile Ile Ala Gln
65                  70                  75                  80

Asp Trp Asp Gly Ile Ile Pro Ala Leu Lys Thr Gly Lys Phe Asp Ala
                85                  90                  95

Ile Val Ala Ala Met Ser Val Thr Pro Glu Arg Ser Glu Gln Val Asp
            100                 105                 110

Phe Ser Glu Pro Tyr Phe Val Asn Ser Leu Val Phe Leu Ala Lys Lys
        115                 120                 125

Gly Ser Asn Phe Asp Pro Ser Ser Thr Asp Ala Ile Asn Asn Ala Lys
    130                 135                 140

Ile Val Ala Gln Arg Ser Thr Ile Ser Ser Gln Trp Leu Thr Gln Thr
145                 150                 155                 160

Tyr Pro Asn Ser Lys Pro Gln Leu Tyr Asp Thr Leu Asp Asn Ala Phe
                165                 170                 175

Ile Asp Leu Gly Asn Glu Arg Ala Asp Ala Met Ile Ser Asp Lys Leu
            180                 185                 190

Pro Ala Leu Thr Trp Leu Ser Ser Asp Leu Gly Gln Asn Phe Glu Ile
        195                 200                 205

Lys Gly Gly Asp Ile Asn Ile Asn Asp Lys Val Ser Ile Ala Val Asp
    210                 215                 220

Lys Gly Asn Thr Ala Leu Leu Gln Lys Phe Asn Glu Ala Leu Ala Ala
225                 230                 235                 240

Ile Lys Ala Asp Gly Thr Tyr Lys Gln Ile Val Ile Lys His Phe Gly
                245                 250                 255

Glu Ala Gly Met Pro Thr Asn Ile Glu
            260                 265
```

```
<210> SEQ ID NO 5
<211> LENGTH: 34
<212> TYPE: DNA
<213> ORGANISM: Artificial
<220> FEATURE:
<223> OTHER INFORMATION: Primer

<400> SEQUENCE: 5
gggacttcca tatgcagtcg cagaacatca gccg                             34

<210> SEQ ID NO 6
<211> LENGTH: 36
<212> TYPE: DNA
<213> ORGANISM: Artificial
<220> FEATURE:
<223> OTHER INFORMATION: Primer

<400> SEQUENCE: 6
attatatagc ggccgcaagc caatgcgtgc catttc                           36

<210> SEQ ID NO 7
<211> LENGTH: 31
<212> TYPE: DNA
<213> ORGANISM: Artificial
<220> FEATURE:
<223> OTHER INFORMATION: Primer

<400> SEQUENCE: 7
ggcagatctt gcagtcgcag aacatcagcc g                                31

<210> SEQ ID NO 8
<211> LENGTH: 33
<212> TYPE: DNA
<213> ORGANISM: Artificial
<220> FEATURE:
<223> OTHER INFORMATION: Primer

<400> SEQUENCE: 8
acgcgtcgac ttaaagccaa tgcgtgccat ttc                              33

<210> SEQ ID NO 9
<211> LENGTH: 38
<212> TYPE: DNA
<213> ORGANISM: Artificial
<220> FEATURE:
<223> OTHER INFORMATION: Primer

<400> SEQUENCE: 9
catttagtat ccatatgtgt agcggtcaaa acgaacaa                         38

<210> SEQ ID NO 10
<211> LENGTH: 39
<212> TYPE: DNA
<213> ORGANISM: Primer

<400> SEQUENCE: 10
caatcttatc tcgagttcaa tattagttgg catacctgc                        39

<210> SEQ ID NO 11
<211> LENGTH: 31
<212> TYPE: DNA
<213> ORGANISM: Artificial
<220> FEATURE:
<223> OTHER INFORMATION: Primer

<400> SEQUENCE: 11
```

-continued

```
ctaggatcct tgtagcggtc aaaacgaaca a                                    31
```

<210> SEQ ID NO 12
<211> LENGTH: 36
<212> TYPE: DNA
<213> ORGANISM: Artificial
<220> FEATURE:
<223> OTHER INFORMATION: Primer

<400> SEQUENCE: 12

```
cagaagcttt tattcaatat tagttggcat acctgc                               36
```